US00PP30429P3

(12) United States Plant Patent
Wang

(10) Patent No.: US PP30,429 P3
(45) Date of Patent: Apr. 23, 2019

(54) ***BROUSSONETIA* PLANT NAMED 'JINHUDIE'**

(50) Latin Name: ***Broussonetia* L'Hér. ex Vent.**
Varietal Denomination: Jinhudie

(71) Applicant: HENAN MINGPIN COLORIZED SEEDLING CO., LTD, Suiping, Henan (CN)

(72) Inventor: Huaming Wang, Henan (CN)

(73) Assignee: HENAN MINGPIN COLORIZED SEEDLING CO., LTD, Suiping, Henan (CN)

( * ) Notice: Subject to any disclaimer, the term of this patent is extended or adjusted under 35 U.S.C. 154(b) by 51 days.

(21) Appl. No.: 15/731,043

(22) Filed: Apr. 11, 2017

(65) Prior Publication Data

US 2017/0311504 P1 Oct. 26, 2017

(51) Int. Cl.
*A01H 5/00* (2018.01)
*A01H 5/12* (2018.01)

(52) U.S. Cl.
USPC ..... Plt./216
CPC ..... *A01H 5/12* (2013.01)

(58) Field of Classification Search
USPC ..... Plt./216
CPC ..... A01H 5/12; A01H 5/00
See application file for complete search history.

*Primary Examiner* — Kent L Bell

(57) ABSTRACT

'Jinhudie' is a distinctive variety of *Broussonetia* Plant, which is characterized by its color of leaves.

7 Drawing Sheets

Genus and species: *Broussonetia* L'Hér. ex Vent.
Variety denomination: 'Jinhudie'.

BACKGROUND OF THE INVENTION

The present invention relates to a new and distinct variety of *Broussonetia* plant, which is given the varietal denomination of 'Jinhudie'.

In April 2006, a mutated *Broussonetia* naturally occurring whole plant was found among *Broussonetia* seedlings in a nursery at Chuxu Village, Suiping County, Henan Province, China. Leaf margins of the mutated *Broussonetia* plant were golden in spring, yellow in summer and golden in autumn, while leaf centers were light green in spring, and dark green in summer as well as autumn. However, leaves of other known seedlings in the same nursery were green. Since the main breeding material of this variety is branches and buds, branches of mutated were then grafted in spring and the mutated plant was reproduced by budding with xylem.

In April 2007, the mutated *Broussonetia* plant was grafted with a rootstock of a wild *Broussonetia* plant and branches of the mutated plant in the same nursery. According to observation, in spring, leaf margins of new-born plant were golden while leaf centers were green. In summer, leaves turned to slight yellow-green with blackish green spots. In autumn, the leaf margins were orange-yellow while leaf centers were yellow-green. All character were stable. In the nursery, except for some species of maple, there were no other varieties. The nursery has excellent land, smooth drainage, and no pollution sources around. The nursery is closed with only one entrance. Average summer maximum temperature at the nursery is 38 degrees Celsius, and average winter minimum temperature is −6 degrees Celsius. Annual average rainfall is 800 mm.

In spring 2008, the grafted plant was asexually reproduced by grafting and cottage. Characteristics thereof were all kept.

From 2009-2013, after generations of reproducing, no atavism or further mutation was observed. Characteristics of the distinct variety were kept stable.

The new and distinct variety of *Broussonetia* plant is not commercially available.

SUMMARY OF THE NEW VARIETY

'Jinhudie' is a bud mutation of *Broussonetia* plant with wide deciduous leaves, whose crown is extended and is oval-shaped or wide oval-shaped. Bark of 'Jinhudie' is smooth, light gray or grayish brown, and without cracking. The whole plant contains milk-like sap. Young branches are densely covered with fine hairs. Single-leaves, which grow alternately and sometimes almost oppositely, are thick papery. The leaves are oval-shaped or wide oval-shaped with acute apexes. Bases of the leaves are rounded, subcordate or skewed. The leaves have serrated margins, and have no crack or 3-5 cracks (more obvious on young branches). Upper surfaces of the leaves are rough and covered with hard hairs. Lower surfaces of the leaves are covered with soft hairs. There are 7-8 pairs of lateral veins. In spring, leaf margins are golden (RHS YELLOW 6C-A) while leaf centers are green (RHS GREEN 140B-A or 141C-A). In summer, leaves turned to slight yellow-green (RHS YELLOW-GREEN N144D-A) with blackish green spots (RHS GREEN 140B-A or 141C-A). In autumn, the leaf margins were orange-yellow (RHS YELLOW 9C-A) while leaf centers were yellow-green (RHS GREEN 140B-A or 141C-A). Crown expends to be ovate to broadly ovate. Bark is smooth. The leaves alternate and sometimes nearly opposite, and are ovate to broadly ovate, wherein a front end portion is acute while a base portion is ovate, subcordate or oblique. Petioles long 3-5 cm, and are densely covered with thick hairs. Stipules are ovate or oblong, and caduceus. Flowers are female. Polythalamic fruits are spherical. Mature fruits are orange-red (RHS ORANGE-RED 30D-A) with nodules thereon. Florescence is from April to May while fruiting from August to September.

BRIEF DESCRIPTION OF THE DRAWINGS

The accompanying colored photographs illustrate the overall appearance of the new and distinct variety of 'Jinhudie'. The descriptions disclosed herein are based upon observations of the plant growth.

DETAILED DESCRIPTION

Figure 1:
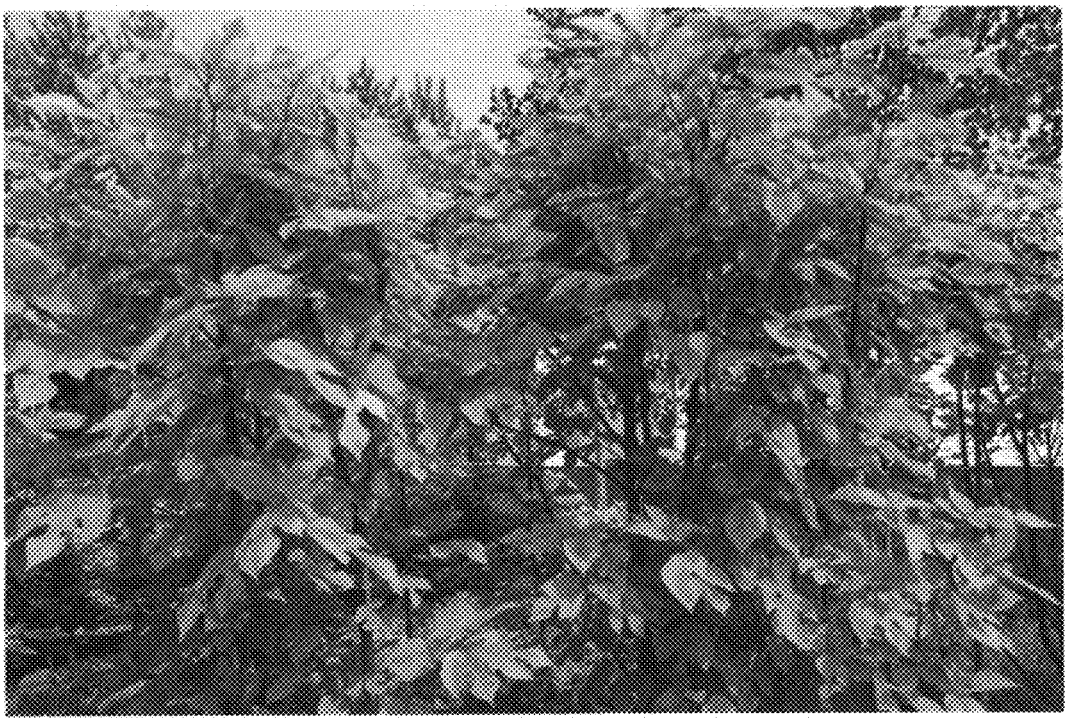
FIG. 1 is a color photograph of the new invention, 'Jinhudie', showing a 2-year plant in the field on Apr. 10, 2010, which is grafted in 2008.
Figure 2:
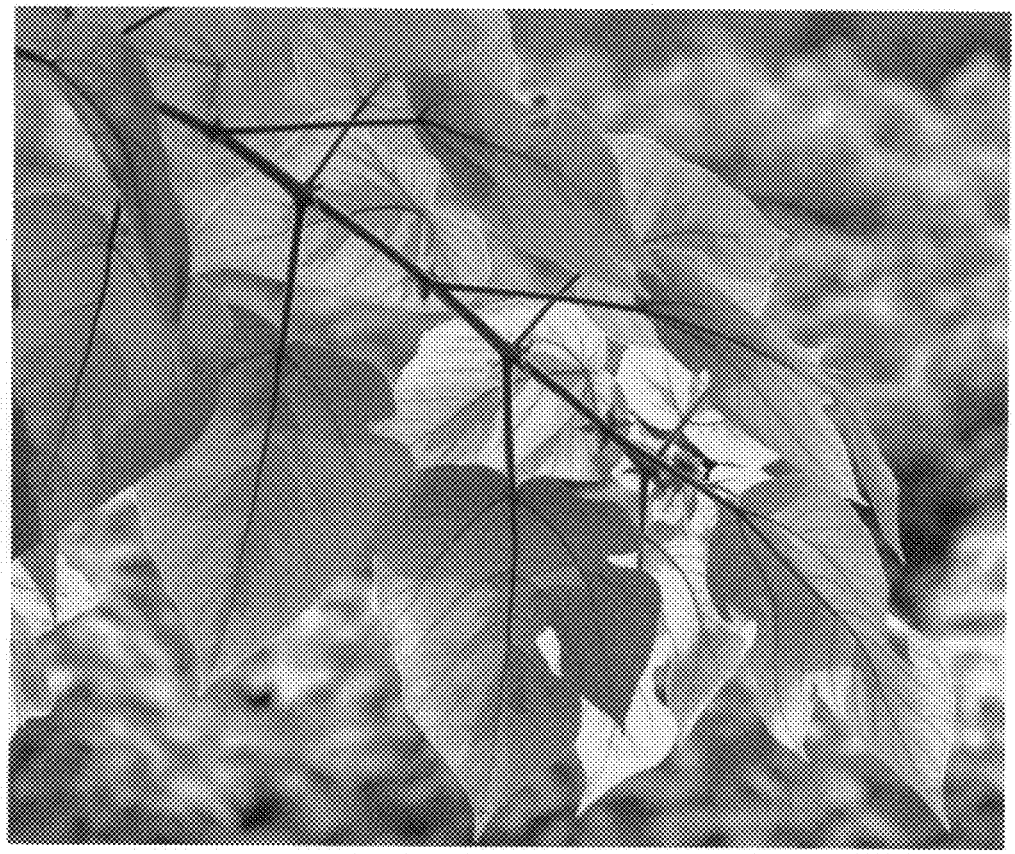
FIG. 2 is a color photograph of the new invention, 'Jinhudie', showing stem of a 3-year plant on Jun. 2, 2011, which is grafted in 2008.
Figure 3:
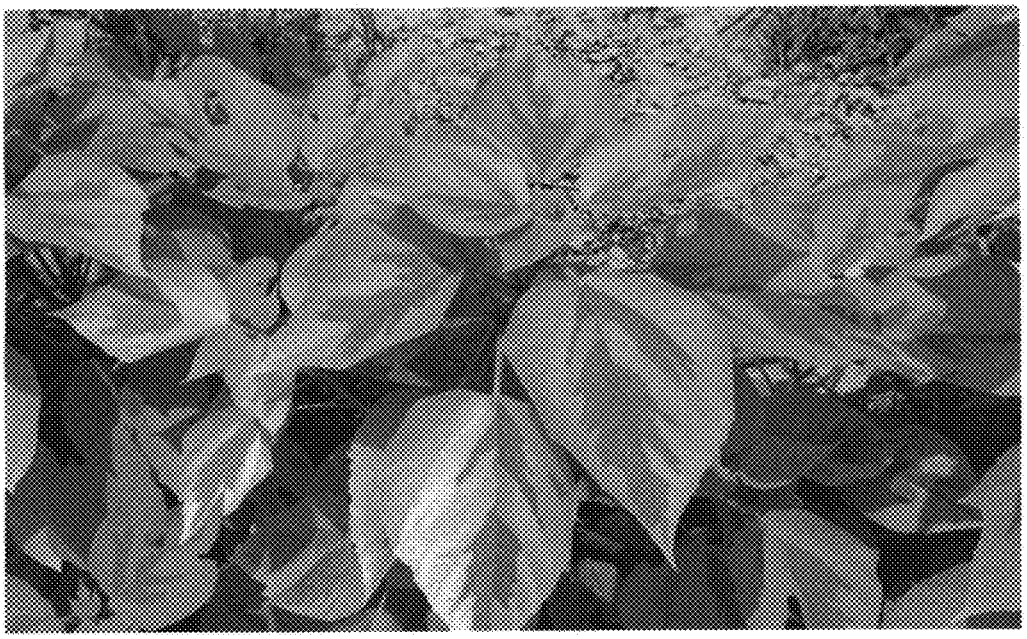
FIG. 3 is a color photograph of the new invention, 'Jinhudie', showing leaves of a 5-month plant in august, which is cut in summer, 2012.
Figure 4:
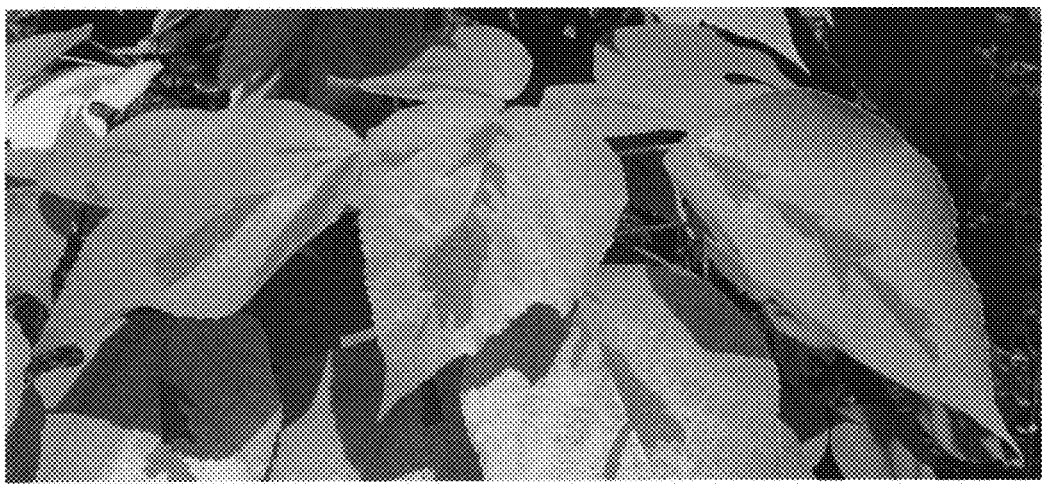
FIG. 4 is a color photograph of the new invention, 'Jinhudie', showing leaves of a 3-year plant on Oct. 23, 2011, which is grafted in 2008.
Figure 5:
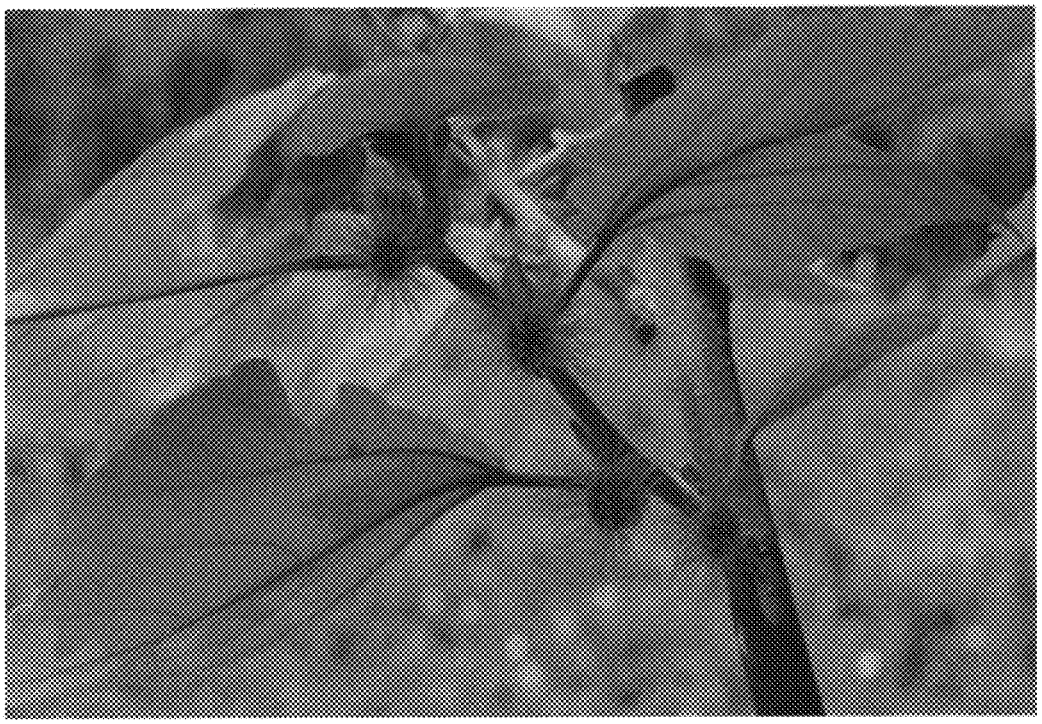
FIG. 5 is a color photograph of the invention, 'Jinhudie', showing the appearance of flowers of a 2-year plant on May 6, 2012.
Figure 6:
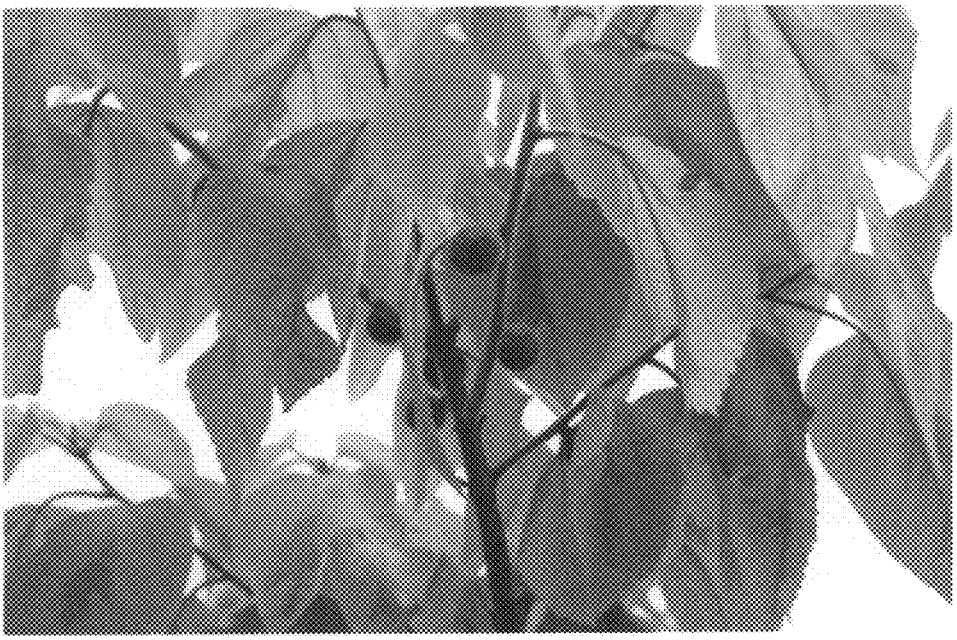
FIG. 6 is a color photograph of the invention, 'Jinhudie', showing the appearance of fruits of a 2-year plant on Jun. 1, 2010.
Figure 7:
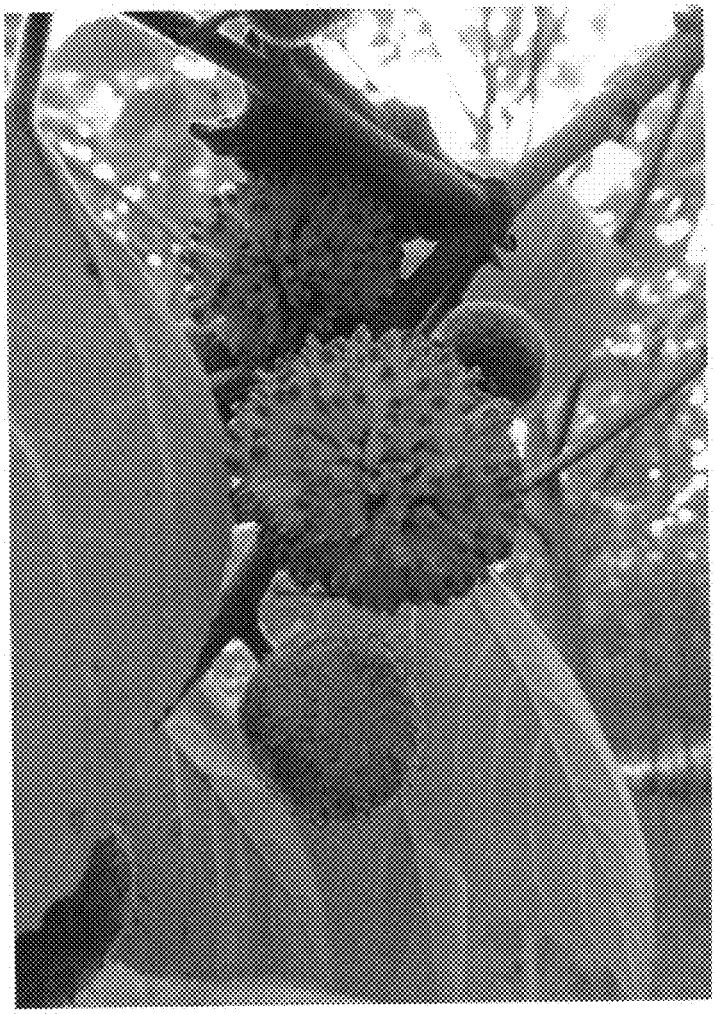
FIG. 7 is a color photograph of the invention, 'Jinhudie', showing the appearance of fruits of a 4-year plant on Jul. 13, 2012.

'Jinhudie' is a bud mutation of *Broussonetia* plant with wide deciduous leaves, whose crown is extended and is oval-shaped or wide oval-shaped. Bark of 'Jinhudie' is smooth, light gray or grayish brown, and without cracking. The whole plant contains milk-like sap. Young branches are densely covered with fine hairs. Single-leaves, which grow alternately and sometimes almost oppositely, are thick papery. The leaves are oval-shaped or wide oval-shaped with acute apexes. Bases of the leaves are rounded, subcordate or skewed. The leaves have serrated margins, and have no crack or 3-5 cracks (more obvious on young branches). Upper surfaces of the leaves are rough and covered with hard hairs. Lower surfaces of the leaves are covered with soft hairs. There are 7-8 pairs of lateral veins. In spring, leaf margins are golden (RHS YELLOW 6C-A) while leaf centers are green (RHS GREEN 140B-A or 141C-A). In summer, leaves turned to slight yellow-green (RHS YELLOW-GREEN N144D-A) with blackish green spots (RHS GREEN 140B-A or 141C-A). In autumn, the leaf margins were orange-yellow (RHS YELLOW 9C-A) while leaf centers were yellow-green (RHS GREEN 140B-A or 141C-A). Crown expends to be ovate to broadly ovate. Bark is smooth. The leaves alternate and sometimes nearly opposite, and are ovate to broadly ovate, wherein a front end portion is acute while a base portion is ovate, subcordate or oblique. Petioles long 3-5 cm, and are densely covered with thick hairs. Stipules are ovate or oblong, and caduceus. Flowers are female. Polythalamic fruits are spherical. Mature fruits are orange-red (RHS ORANGE-RED 30D-A) with nodules thereon. Florescence is from April to May while fruiting from August to September.

'Jinhudie' is a distinctive variety of *Broussonetia* plant, which is able to grow in north, center, south, southwest, and northwest of China, mainly in the Yellow River area, the Yangtze River area and the Pearl River Basin area. The plant grows better in the south of China.

'Jinhudie' is a strong phototropism tree species, whose adaptability is particularly strong. The plant has strong resistance to dry-cold and dry and damp-hot climates, and is able to grow in acidic soil, neutral soil and limestone mountain area due to resistance to drought and barren. The plant grows well at both waterside and wetlands. Roots of the plant are shallow and lateral, which are widely distributed and rapidly grow. 'Jinhudie' has strong abilities in budding and tillering, with strong resistance to pruning and pollution.

Reproducing methods of 'Jinhudie' are mainly graft and cottage. For grafting, whip, cleft and budding (with xylem) are mainly used, while tillering and laying reproducing are also acceptable. For grafting, new-born *Broussonetia* plant is used as a rootstock. In spring, cleft or budding with xylem should be adapted for reproducing. In summer, large-square budding is used for reproducing. For cottage, young summer branches are mainly used, wherein half-xylem young branches with a length of 10-15 cm are cut and inserted into seedling device. With a full-light cottage technology, rooting is extremely fast.

Specifically, branch-graft in spring has a highest survival rate. Every year, in March or before 'Jinhudie' is budded, branches born that year are selected. The branches are cut into about 5 cm long, and bottoms are chamfered, which contains 2-3 buds. Next, the rootstock (with a roughness of between 0.7-1) is cut off flatly, and then vertically cut near one side. The graft material is aligned with one side of the rootstock layer, clamped, and wrapped with a graft plastic film, wherein the buds are left outside. After new leaves are grown, green branches of common species are removed from the rootstocks, so as to the branches of 'Jinhudie' grow rapidly. After the plant grows to 2 meters high, it is planted at a row spacing of 3 meters*4 meters. After 3-4 years, trunks of 'Jinhudie' can grow to a diameter of 8 cm and can be used in greening of parks or scenic spots.

'Jinhudie' can be cultivated and rapidly grow in both spring and autumn. During growth, trimming is needed. The plant is not suitable for growing at low areas which are like to suffer water logging.

'Jinhudie' is particularly adaptable, and resistant of dry, cold, hot and humid climates. The plant can grow in acid soil, neutral soil and limestone mountains, with resistant to drought and thinness. The plant grows well in low-water wetlands.

'Jinhudie' rarely suffers from pests and diseases. However, in some particular regions having trunk-attacking pests such as longhorned beetles and jewel beetles, preventing is needed.

TABLE 1 comparison between 'Jinhudie' and similar species.

| similar species | features of similar species | features of 'Jinhudie' |
|---|---|---|
| paper mulberry | dioecism | female |
| | single color | complex color |
| | young leaf is mainly green | young leaf is mainly yellow |
| | no secondary color | secondary color is green |

TABLE 1-continued comparison between 'Jinhudie' and similar species.

| similar species | features of similar species | features of 'Jinhudie' |
|---|---|---|
| | no distribution of secondary color | secondary color is distributed at center |

These features and other characteristics of the plant are apparent from the figures.

What is claimed is:

1. A new and distinct variety of *Broussonetia* Plant named 'Jinhudie', substantially as described and illustrated.

* * * * *